(12) United States Patent
Gaillard

(10) Patent No.: US 7,665,606 B2
(45) Date of Patent: Feb. 23, 2010

(54) CLAMP-ON TRAY FOR NEUROSURGICAL PATTIES

(76) Inventor: Johnnie M. Gaillard, 711 S. Purdom St., Kokomo, IN (US) 46901

( * ) Notice: Subject to any disclaimer, the term of this patent is extended or adjusted under 35 U.S.C. 154(b) by 168 days.

(21) Appl. No.: 11/811,463

(22) Filed: Jun. 11, 2007

(65) Prior Publication Data

US 2008/0000910 A1 Jan. 3, 2008

Related U.S. Application Data

(60) Provisional application No. 60/814,620, filed on Jun. 16, 2006.

(51) Int. Cl.
*B65D 85/00* (2006.01)
(52) U.S. Cl. .......... 206/363; 206/438; 206/372
(58) Field of Classification Search .......... 206/438, 206/210, 234, 63.5, 63.3, 369, 366, 372, 206/363, 362, 370, 557, 562; 248/229.15, 248/229.25
See application file for complete search history.

(56) References Cited

U.S. PATENT DOCUMENTS

| | | | | |
|---|---|---|---|---|
| 1,658,891 A | * | 2/1928 | Gauck | 211/119.012 |
| 1,974,213 A | * | 9/1934 | Gilbert | 211/88.01 |
| 3,301,406 A | * | 1/1967 | Scott | 211/88.01 |
| 3,366,230 A | * | 1/1968 | Loran | 206/63.5 |
| 3,949,880 A | * | 4/1976 | Fortunato | 211/119.003 |
| 4,793,483 A | | 12/1988 | Holmes | |
| 5,352,218 A | * | 10/1994 | Buckley et al. | 604/407 |
| 5,381,896 A | * | 1/1995 | Simons | 206/370 |
| 5,511,674 A | | 4/1996 | Boyd et al. | |
| 5,520,689 A | * | 5/1996 | Schlapfer et al. | 606/270 |
| 5,725,111 A | * | 3/1998 | Choi | 211/119.1 |
| 6,364,262 B1 | * | 4/2002 | Gibson et al. | 248/229.24 |
| 6,622,861 B2 | | 9/2003 | Kissling | |
| 6,969,498 B1 | * | 11/2005 | Riley | 422/300 |
| 2001/0033890 A1 | * | 10/2001 | Kissling | 427/2.31 |

* cited by examiner

*Primary Examiner*—Ehud Gartenberg
*Assistant Examiner*—Andrew Perreault
(74) *Attorney, Agent, or Firm*—Frank D Lachenmaier

(57) ABSTRACT

In accordance with the present invention, a Clamp-On Tray for Neurosurgical Patties comprises a rectangular tray having a well at each end, parallel individual channels for the patty strings running between the wells and c-clamps mounted on one side for attaching to a MAYO stand encased in sterilized covering material.

4 Claims, 4 Drawing Sheets

CLAMP-ON TRAY FOR NEUROSURGICAL PATTIES

FEDERALLY SPONSORED RESEARCH

None

SEQUENCE LISTING OR PROGRAM

None

BACKGROUND

1. Field of Invention

This invention relates generally to accessory trays for use in surgery and more particularly, trays for presenting neurosurgical patties of absorbent material in a convenient arrangement for a surgeon during an operation.

2. Discussion of Prior Art

The MAYO stand is a movable stand that cantilevers a tray over the body of the patient in surgery. This tray contains all the surgical instruments required for a given surgical procedure and the space is relatively limited on its top surface. This MAYO stand and tray are covered with a sterilized paper, gauze or cloth boot to provide a sterile environment for the operation.

Neurosurgery is surgery of the central nervous system which requires very delicate tissue to be dissected, retracted and possibly removed. Pads of absorbent material called neurosurgical patties, sometimes soaked in a saline or anti-coagulant material, need to be presented to the surgeon in a convenient and secure manner. The surgeon utilizes them to absorb or retain fluids such as blood and other brain fluids that result from the dissection process. Once they absorb blood or other fluids it becomes very difficult to distinguish them from the adjacent tissues. Thus, these patties typically have long sterilized strings attached to them, the ends of which are left outside the body for easy removal of the patties after the surgical procedure is complete.

Several devices are currently, but unsatisfactorily, in use today to present such patties to the surgeon. They used to be called Cottonoid Boards, but today are referred to as neurosurgical patty boards or trays.

Some were clipped onto the surgical drape that covers the rest of the patient's body except for the surgical site, as in U.S. Pat. No. 4,793,483 to Holmes. These were held on with flat jawed alligator clips which were easily dislodged if bumped by the surgeon or the nurse, causing unwarranted delays in the surgery while new sterile patties were attained, soaked and presented.

Others were clipped or attached to the MAYO stand tray using alligator clips that were easily dislodged. Still others were clasped, latched or connected to the MAYO frame or tray in a manner that could easily tear the sterile paper boot that covers the MAYO stand or tray such as in U.S. Pat. No. 5,511,674 to Boyd et al.

Some had no grooves or channels for keeping the strings separated and others had no well for keeping the patties moist during surgery Finally, U.S. Pat. No. 6,622,861 B2 to Kissling shows stackable trays for delivery of the patties that are adhesively adhered to the sterile cover on the top of the MAYO stand and to the empty tray or trays if multiple trays of pads are required. Their stackable nature only requires using up one tray's footprint, but they still occupy valuable space on the top surface of the covered MAYO stand.

OBJECTS

The Clamp-On Tray for Neurosurgical Patties embodied in this invention resolves the above mentioned problems by its unique shape and clamping mechanisms.

It is an objective of this invention that it clamp securely onto a MAYO stand tray without the risk of tearing the sterile paper, gauze or cloth boot surrounding the MAYO stand.

It is also an objective of this invention that it keep the strings attached to neurosurgical patties from tangling and make the patties easy to remove from the tray with standard surgical forceps.

Another objective of this invention is that it allows the neurosurgical patties to be kept in a moistened state with the appropriate solution throughout the duration of the surgical procedure. Further objects and advantages will become apparent from a consideration of the drawings and ensuing description.

SUMMARY

In accordance with the present invention a Clamp-On Tray for Neurosurgical Patties comprises a rectangular tray having a well at each end and parallel individual channels for the patty strings running between the wells and pivotally mounted C-clamps on one side for attaching to a MAYO stand. The tray clamps have no motion relative to sterile gauze surface and as such will not tear the gauze.

DRAWINGS

In order that the invention may be more fully understood it will now be described by way of example, with reference to the accompanying exemplary drawings in which.

REFERENCE NUMERALS

The same reference numbers are used to refer to the same or similar parts in the various views.

| | |
|---|---|
| 10 | Clamp-On Tray for Neurosurgical Patties |
| 12 | c-clamp assembly |
| 14 | c-clamp pivot mount |
| 18 | neurosurgical patty locating string (not part of this invention) |
| 20 | neurosurgical patty string channel |
| 22 | neurosurgical patty string pickup notch |
| 24 | rear neurosurgical patty well |
| 26 | solution (not part of this invention) |
| 28 | MAYO Stand (not part of this invention) |
| 30 | MAYO Stand shroud (not part of this invention) |
| 32 | free floating anvil |
| 34 | jack screw handle |

-continued

| | |
|---|---|
| 36 | stationary anvil |
| 38 | flat surface |
| 40 | bottom surface of the tray |
| 42 | front side |
| 44 | back side |
| 46 | sidewall |
| 48 | jack screw |
| 50 | threaded collar |
| 52 | ½ in × 1 in neurosurgical patty (not part of this invention) |
| 54 | ½ in × ½ in neurosurgical patty (not part of this invention) |
| 56 | 1 in × 1 in neurosurgical patty (not part of this invention) |
| 58 | ⅜ in × ¾ in neurosurgical patty (not part of this invention) |
| 60 | ⅜ in × ⅜ in neurosurgical patty (not part of this invention) |
| 62 | 1 in × 3 in neurosurgical patty (not part of this invention) |
| 64 | ½ in × 1½ in neurosurgical patty (not part of this invention) |
| 66 | ¼ in × ¼ in neurosurgical patty (not part of this invention) |
| 68 | ¼ in × ⅛ in neurosurgical patty (not part of this invention) |
| 70 | front neurosurgical patty well |

DESCRIPTION

Figure 1:
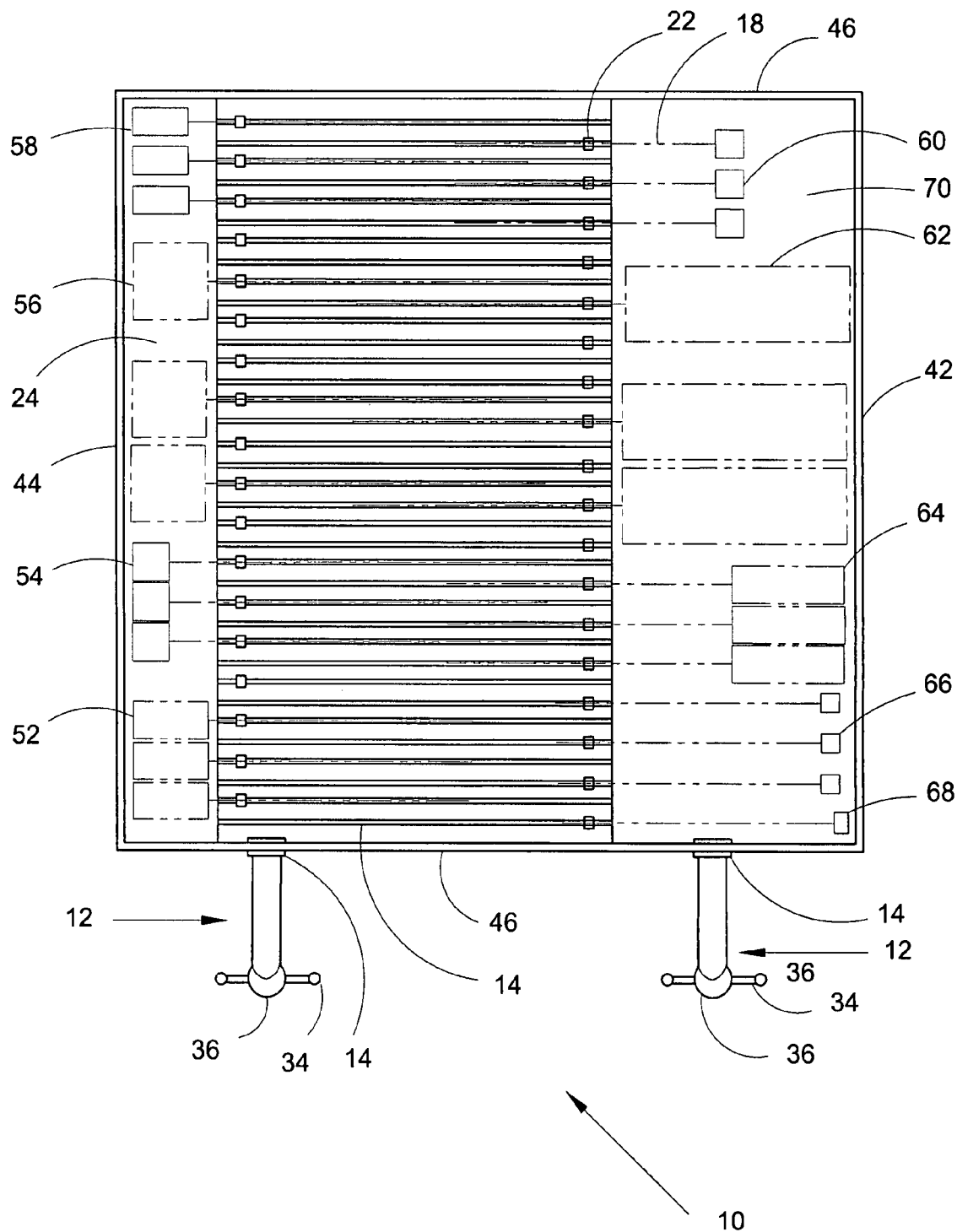
FIG. 1 is a top view.
Figure 2:
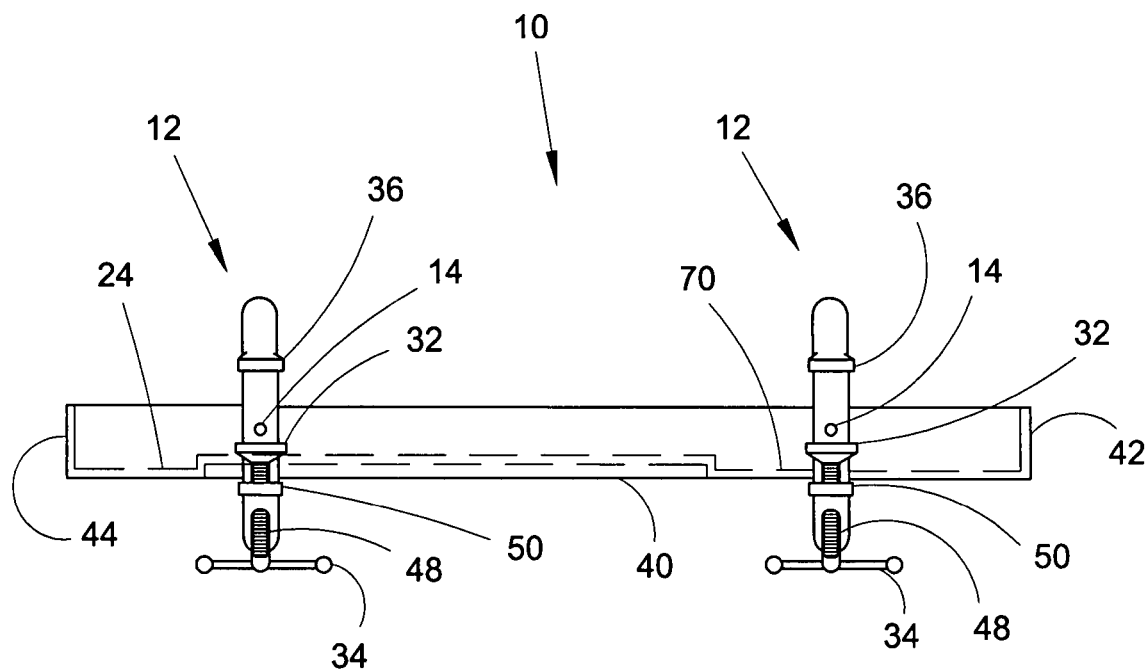
FIG. 2 is a front view.
Figure 3:
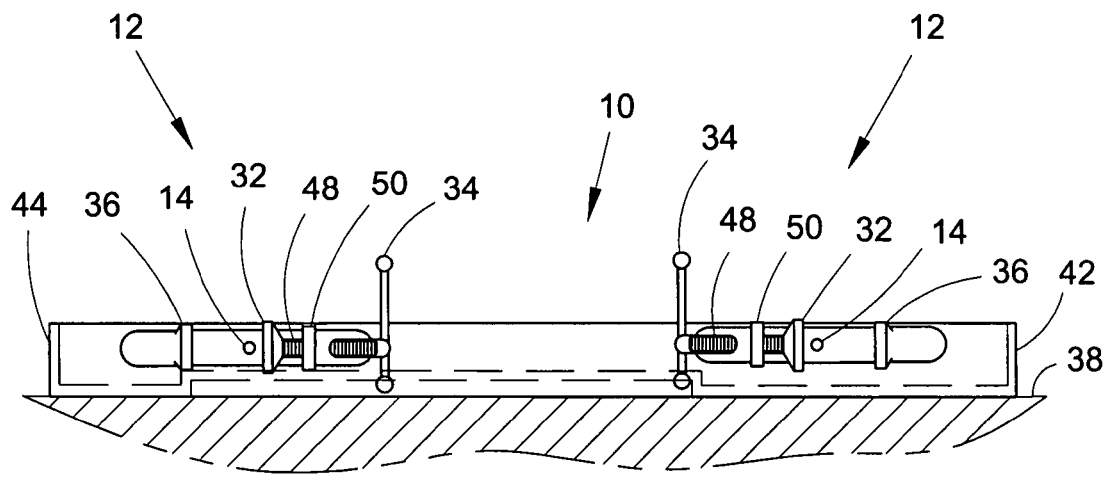
FIG. 3 is a front view showing the c-clamps in their rotated position for seating on a flat surface or table.
Figure 4:
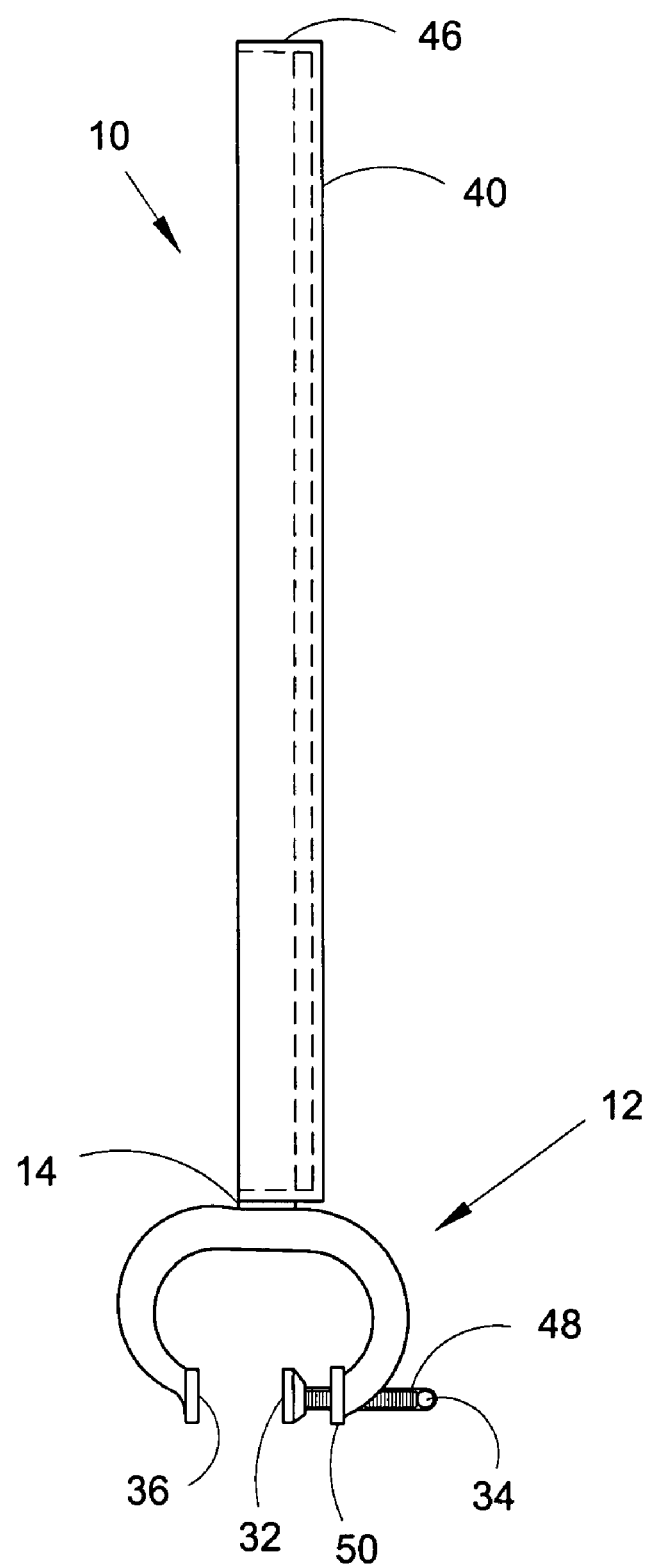
FIG. 4 is a side view.
Figure 5:
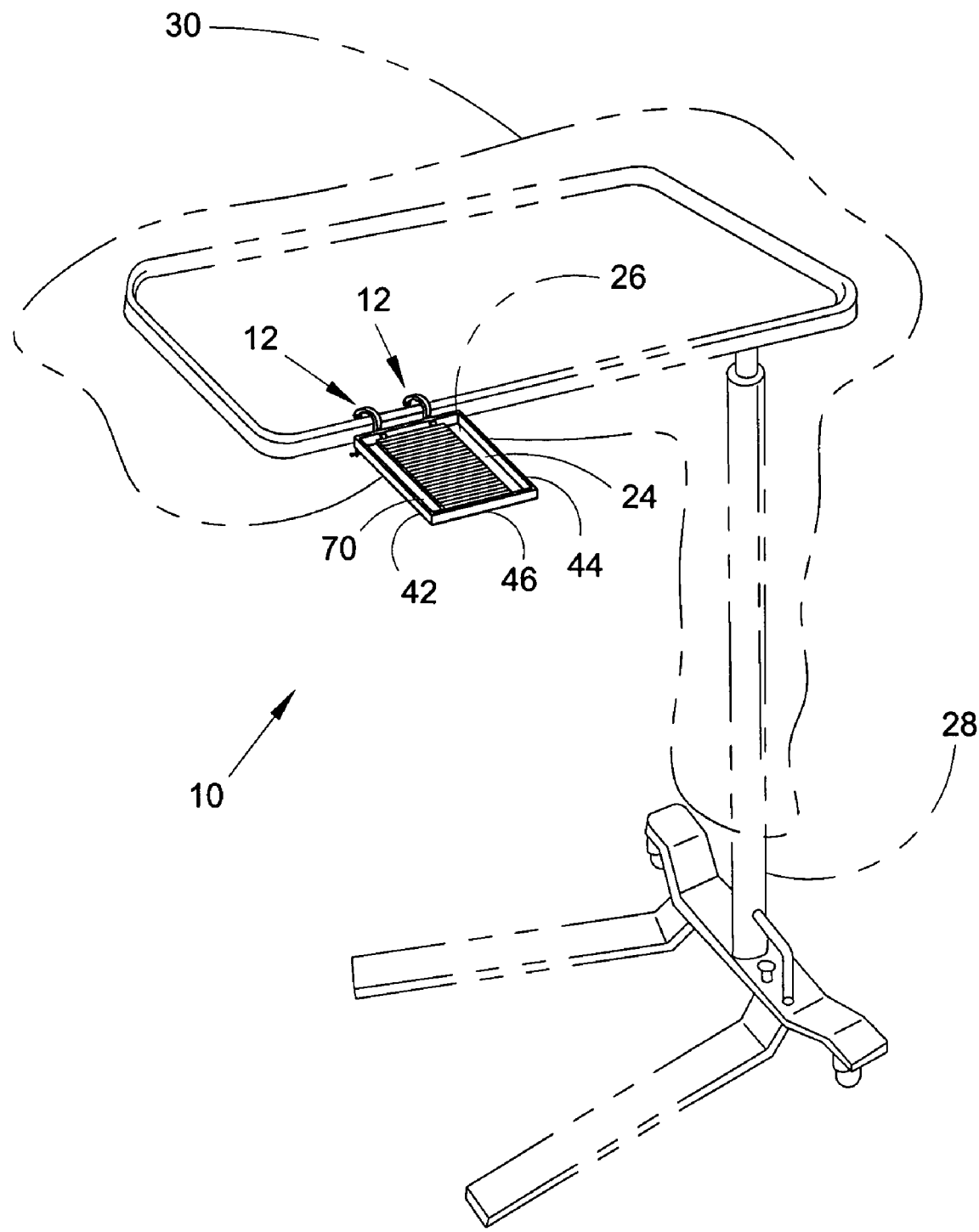
FIG. 5 is perspective view showing the Clamp-On Tray for Neurosurgical Patties clamped to a MAYO stand shrouded with a sterilized paper boot.

A preferred embodiment of Clamp-On Tray for Neurosurgical Patties 10 is shown in FIGS. 1, 2, 4, 5. It is an objective of this Invention to clamp securely onto MAYO stand 28 without risk of tearing the sterile paper, gauze or cloth boot or shroud 30 surrounding MAYO stand 28. It utilizes two c-clamp assemblies 12 that have stationary anvils 36 at the top of the c and free floating anvils 32 mounted on the tops of jack screws 48 which turn through threaded collars 50 on the bottom of the c as shown in FIG. 3. C-clamp assemblies 12 will not tear shroud 30 because there is no relative motion between shroud 30 and anvils 36 and 32. C-clamp assemblies 12 provide a secure attachment for Clamp-On Tray for Neurosurgical Patties 10 to MAYO stand 28 as shown in FIG. 5. Clamp-On Tray for Neurosurgical Patties 10 is not going to be dislodged and drop the sterile patties 16 onto a non-sterile surface if it is bumped during surgery. C-clamp assemblies 12 are secured to sidewall 46 of Clamp-On Tray for Neurosurgical Patties 10 in a pivotal fashion so that when it is desired to place Clamp-On Tray for Neurosurgical Patties 10 on a flat surface 38 instead of fastening it to the side of MAYO stand 28 or to stack multiple trays, c-clamp assemblies 12 can simply be rotated about c-clamp pivot mount 14 into a parallel plane with the bottom surface of tray 49 as shown in FIG. 3.

Clamp-On Tray for Neurosurgical Patties 10 contains individual channels 20 for each string 18 attached to patties 52 through 68 to keep strings 18 that are attached to neurosurgical patties 52 through 68 from tangling, and making patties 52 through 68 easy to remove from Clamp-On Tray for Neurosurgical Patties 10 with standard surgical forceps (not shown). Toward the well end of channels 20 are neurosurgical patty string pickup notches 22 that expose strings 18 with sufficient clearance that typical surgical forceps (not shown) can grasp string 18 and remove and place patties 52 through 68 at the desired location during the surgical procedure.

Neurosurgical patty wells 24 and 70 are depended from the bottom surface of Clamp-On Tray for Neurosurgical Patties 10 at both front end 42 and rear end 44 and neurosurgical patties 52 through 68 are placed into them. Neurosurgical patty wells 24 and 70 accept solution 26 for keeping neurosurgical patties 52 through 68 moistened with appropriate solution 26 as shown in FIG. 5.

Clamp-On Tray for Neurosurgical Patties 10 can be molded from an engineering thermoplastic that is sterilizable for single use, throw away containers or made from stainless steel if multiple uses are contemplated. Various sizes and shapes of trays are within the contemplated design for this invention such as a 10 inch long by 10 inch wide by ¾ inches deep. Well lengths are sized to fit the absorbent patties that range in size from ¼×¼ inches to 1×3 inches required for given surgeries.

What is claimed as invention is:

1. A tray for clamping on a MAYO stand encased in sterilized covering material or shroud for presentation of neurosurgical patties with attached locating strings for a surgeon's use during a surgical procedure comprising:
   a) a rectangular tray with a front side, a back side, sidewalls, and a bottom surface;
   b) two c-clamp assemblies mounted to one of said sidewalls comprising:
      a c frame;
      a stationary clamp anvil at the top opening in said c frame;
      a threaded collar at the bottom of the opening in said c frame;
      a jack screw with a top end and a bottom end, threaded through said collar;
      a floating anvil pivotally attached to said top end of said jack screw; and
      a handle slidably attached to said bottom end of said jack screw such that when said handle is rotated in a clockwise motion, said jack screw is advanced, clamping said MAYO stand tray encased in sterilized covering material between said stationary anvil and said floating anvils with no relative motion between said anvils and said sterilized covering material;
   c) two wells for said neurosurgical patties depended from said bottom surface, one adjacent to said front side of said rectangular tray and one adjacent to said back side of said rectangular tray in which an appropriate solution is accepted to keep said patties moist during surgery; and
   d) a plurality of parallel channels between said wells facilitated to receive said locating strings with a clearance notch for standard surgical forceps to grasp said locating strings to facilitate picking and placing said neurosurgical patties attached to said locating strings.

2. The tray of claim 1 for clamping on a MAYO stand encased in sterilized covering material or shroud for presentation of neurosurgical patties with attached locating strings for a surgeon's use during a surgical procedure wherein said tray is made from a sterilizable thermoplastic material.

3. The tray of claim 1 for clamping on a MAYO stand encased in sterilized covering material or shroud for presentation of neurosurgical patties with attached locating strings for a surgeon's use during a surgical procedure wherein said tray is made from a stainless steel material.

4. The tray of claim 1 for clamping on a MAYO stand encased in sterilized covering material or shroud for presentation of neurosurgical patties with attached locating strings for a surgeon's use during a surgical procedure wherein said c-clamp assemblies are pivotally mounted on said side of said tray and can be rotated 90 degrees, eliminating protrusions above and below side of said tray.

* * * * *